US00PP13473P2

(12) United States Plant Patent
Bradford

(10) Patent No.: US PP13,473 P2
(45) Date of Patent: Jan. 14, 2003

(54) PEACH TREE NAMED 'SUGAR PRINCESS'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,019

(22) Filed: Dec. 13, 2001

(51) Int. Cl.[7] ..... A01H 5/00
(52) U.S. Cl. ..... Plt./198
(58) Field of Search ..... Plt./198

(56) References Cited

U.S. PATENT DOCUMENTS

PP7,066 P 12/1989 Bradford ..... Plt./198

*Primary Examiner*—Bruce R. Campell
*Assistant Examiner*—W C Haas

(57) ABSTRACT

The present invention relates to a peach tree, *Prunus persica*, and more particularly to a new and distinct variety broadly characterized by a medium size, vigorous, hardy, self-fertile, productive and regular bearing tree. The fruit matures under the ecological conditions described approximately the third week in July, with first picking on Jul. 13, 2001. The fruit is uniformly large in size, very good in flavor, globose in shape, freestone in type, firm in texture, yellow in flesh color, and mostly red in skin color. The variety was developed as a first generation cross using 'Diamond Princess' (U.S. Plant Pat. No. 7,066) yellow flesh peach as the selected seed parent and an unnamed white flesh peach as the selected pollen parent.

1 Drawing Sheet

BOTANICAL CLASSIFICATION

*Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'SUGAR PRINCESS'. The present variety was hybridized by me in 1992, grown as a seedling on its own root in my greenhouse, and transplanted to a cultivated area of our experimental orchard at Bradford Farms near Le Grand, Calif. in Merced County (San Joaquin Valley). It was developed as a first generation cross using 'Diamond Princess' (U.S. Plant Pat. No. 7,066) yellow flesh peach as the selected seed parent and an unnamed white flesh peach as the selected pollen parent. Subsequent to origination of the present variety of peach tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Diamond Princess' (U.S. Plant Pat. No. 7,066) peach, by producing freestone peaches that are globose in shape, firm in texture, and mostly red in skin color, but is distinguished therefrom and an improvement thereon by producing fruit that is subacid instead of acid in flavor, that is larger in size, and that matures about two weeks later.

DRAWING

The accompanying photograph exhibits four whole fruits positioned to display the characteristics of the skin color and form, one fruit divided around the suture plane to reveal the flesh and stone, and typical leaves.

POMOLOGICAL CHARACTERISTICS

Referring now more specifically to the pomological chgaracteristics of this new and distinct variety of peach tree, the following has been observed under the ecological conditions prevailing near Le Grand, Merced County (San Joaquin County), Calif., and was developed at the state of firm ripe on Jul. 16, 2001, on the original tree during its ninth growing season. All major color code designations are by reference to the Inter-Society Color Council, National Bureau of Standards. Common color names are also used occasionally.

Tree

Size: Medium, reaching and maintaining a height of 12' [3.66 m.] after nine growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase formed.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 5" [127.0 mm.] after the ninth growing season.

*Texture.*—Slightly shaggy.
*Bark color.*—Brownish gray [64. brGray].
*Lenticels.*—Numerous. Color: Moderate yellowish brown [77. m.yBr]. Size: Small, 3/16" to 7/16" [4.8–11.1 mm.].

Branches:
*Size.*—Diameter of scaffold is 2½" [64 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older Wood: Grayish brown [61. gy.Br].
*Lenticels.*—Numerous. Color: Moderate orange yellow [71. m.OY]. Size: Small, 1/16" to 3/16" [1.6–4.8 mm.].

Leaves:
*Size.*—Large. Average Length: 5¾" [146 mm.]. Average width: 1 7/16" [37 mm.].
*Arrangement.*—Alternate.
*Thickness.*—Medium.
*Form.*—Elliptical.
*Apex.*—Acuminate.
*Base.*—Acute with an angle of 70 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: Medium, 7/16" [11.1 mm.]. Average Diameter: Medium, 1/16" [1.6 mm.]. Color: Moderate yellow green [120. m.YG].
*Stipules.*—Number: 2 per bud, up to 6 per growing tip. Average Length: ¼" [6.4 mm.]. Color: Light yellow green [119.l.YG] when growing.
*Glands.*—Number: 2 to 4 per leaf. Position: Alternate, usually a pair on the petiole and the rest on the base of the leaf blade. Size: Small. Form: Reniform. Color: Grayish reddish orange [39. gy.rO].
*Leaf buds.*—Pointed.

Flower buds:
*Hardiness.*—Hardy, with respect to central California winters.
*Diameter.*—Typically ⅜" [9.5 mm.] 1 week before bloom.
*Length.*—Typically ¾" [19.1 mm. ] 1 week before bloom.
*Form.*—Not appressed.
*Surface.*—Pubescent.
*Color.*—Moderate purplish red [258. m.pR].

Flowers: Perfect, complete, perigynous, usually a single pistil, typically thirty or more stamens, five sepals and petal locations alternately positioned.
*Type.*—Showy.
*Average flower diameter.*—1 9/16" [39.7 mm.].
*Number of petals.*—Usually five, very few doubles.
*Petal shape.*—Rounded.
*Petal margin.*—Slightly wavy.
*Average petal diameter.*—⅝" [15.9 mm.].
*Average petal length.*—1 1/16" [17.5 mm.].
*Petal apex.*—Rounded.
*Petal base.*—Rounded to slightly obtuse.
*Petal color.*—Light purplish pink [249. l.pPk].
*Anther color.*—Moderate red [15. m.R].
*Stigma color.*—Light yellow green [119. l.YG].
*Sepal color.*—Dark purplish red [259. d.pR].
*Sepal length.*—3/16" [5 mm.].
*Sepal width.*—3/16" [5 mm.].
*Average pistil length.*—9/16" [14.3 mm.].
*Average stamen length.*—⅝" [15.9 mm.].
*Fragrance.*—Moderate when nectar is present.
*Blooming period.*—Medium to slightly early when compared with other varieties.
*Onset of bloom.*—One percent on Feb. 23, 2001.
*Date of full bloom.*—Mar. 6, 2001.
*Duration of bloom.*—One to two weeks, dependent on ambient temperature.
*Number per cluster.*—Generally 1, occasionally 2 or more.

FRUIT

Maturity when described: Hard ripe, Jul. 15, 2000.
Date of first picking: Jul. 13, 2000.
Date of last picking: Jul. 23, 2000.

Size: Uniform, large.
*Average diameter axially.*—3 1/16" [78 mm.].
*Average diameter across suture plane.*—3 3/16" [81 mm.].
*Typical weight.*—9.9 ounces [280 grams].

Form: Uniform, very slightly asymmetrical, globose and slightly compressed axially and towards the suture.
*Longitudinal section form.*—Roundish, with slight axial compression.
*Transverse section through diameter.*—Roundish, protruding at the suture.

Suture: An inconspicuous line extending from the base and discontinuing slightly past the apex with virtually no depression at the apex.

Ventral surface: Rounded, with a bulge along suture line between, but not including, the apex and base.

Lips: None.

Cavity: Flaring, elongated in the suture plane, suture showing on both sides, Brilliant orange yellow [67. brill.OY] stem markings typical.
*Depth.*—⅝" [15.9 mm.].
*Breadth.*—1 1/16" [27.0 mm.].

Base: Somewhat truncate, cuneate when viewed parallel to the suture.

Apex: Rounded.

Pistil point: Apical, less than 1/32" [0.8 mm] in length.

Stem: Medium.
*Average length.*—⅜" [9.5 mm.].
*Average width.*—3/16" [4.8 mm.].

Skin:
*Thickness.*—Thin.
*Texture.*—Pubescent.
*Tenacity.*—Tenacious to flesh.
*Astringency.*—Nonastringent.
*Tendency to crack.*—None observed.
*Color.*—Dark red [16. d.R] over a Deep reddish orange [36. deep rO] background color with some Brilliant yellow [83. brill.Y] areas where shielded from sunlight.

Down: Scant, does not roll up when rubbed.

Flesh:
*Color.*—Vivid yellow [82. v.Y] from skin to within ⅜" [9.5 mm.] of the stone, Deep red [13. deep R] streaking near the stone.

*Surface of pit cavity.*—Deep red [13. deep R] fibers cleanly detaching from the stone.
*Amygdalin.*—Wanting.
*Juice.*—Abundant, rich.
*Texture.*—Firm, tough.
*Fibers.*—Abundant, fine.
*Ripens.*—Earliest at the apex and along the cheeks.
*Flavor.*—Subacid and mild, averaging 14 brix.
*Aroma.*—Very slight.
*Eating quality.*—Good.

STONE

Type: Freestone.
Average width: 1⅛" [28.6 mm.].
Average length: 1¼" [31.8 mm.].
Average breadth: 13/16" [20.6 mm.].
Average pit wall thickness: ¼" [6.4 mm.].
Form: Oval, slightly wider towards apex.
Hilum: Narrow.
Base: Straight.
Apex: Acute, ⅛" [3.2 mm] tip forming an angle of 75 degrees.
Sides: Equal.
Surface: Nearly horizontal furrows toward the apex curving toward the Base, pitted throughout.
Ridges: Jagged toward the base.
Color: Deep brown [56. deep Br].
Tendency to split: Slight.
Kernel:
*Form.*—Oval.
*Pellicle color.*—Strong brown [55. s.Br].
*Skin color.*—Light yellow [86. l.Y] when first exposed.
*Vein color.*—Strong orange yellow [68. s.OY].
*Taste.*—Bitter.
*Viable.*—Yes.
*Average width.*—9/16" [14.3 mm.].
*Average length.*—11/16" [17.5 mm.].
*Amygdalin.*—Abundant.

USE

Market: Fresh market, long distance shipping, backyard grower.
Keeping quality: Good. Fruit quality observed to remain in good condition after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its selected seed parent, 'Diamond Princess' (U.S. Plant Pat. No. 7,066) peach, by producing freestone peaches that are globose in shape, firm in texture, and mostly red in skin color, but is distinguished therefrom and an improvement thereon by producing fruit that is subacid instead of acid in flavor, that is larger in size, and that matures about two weeks later.

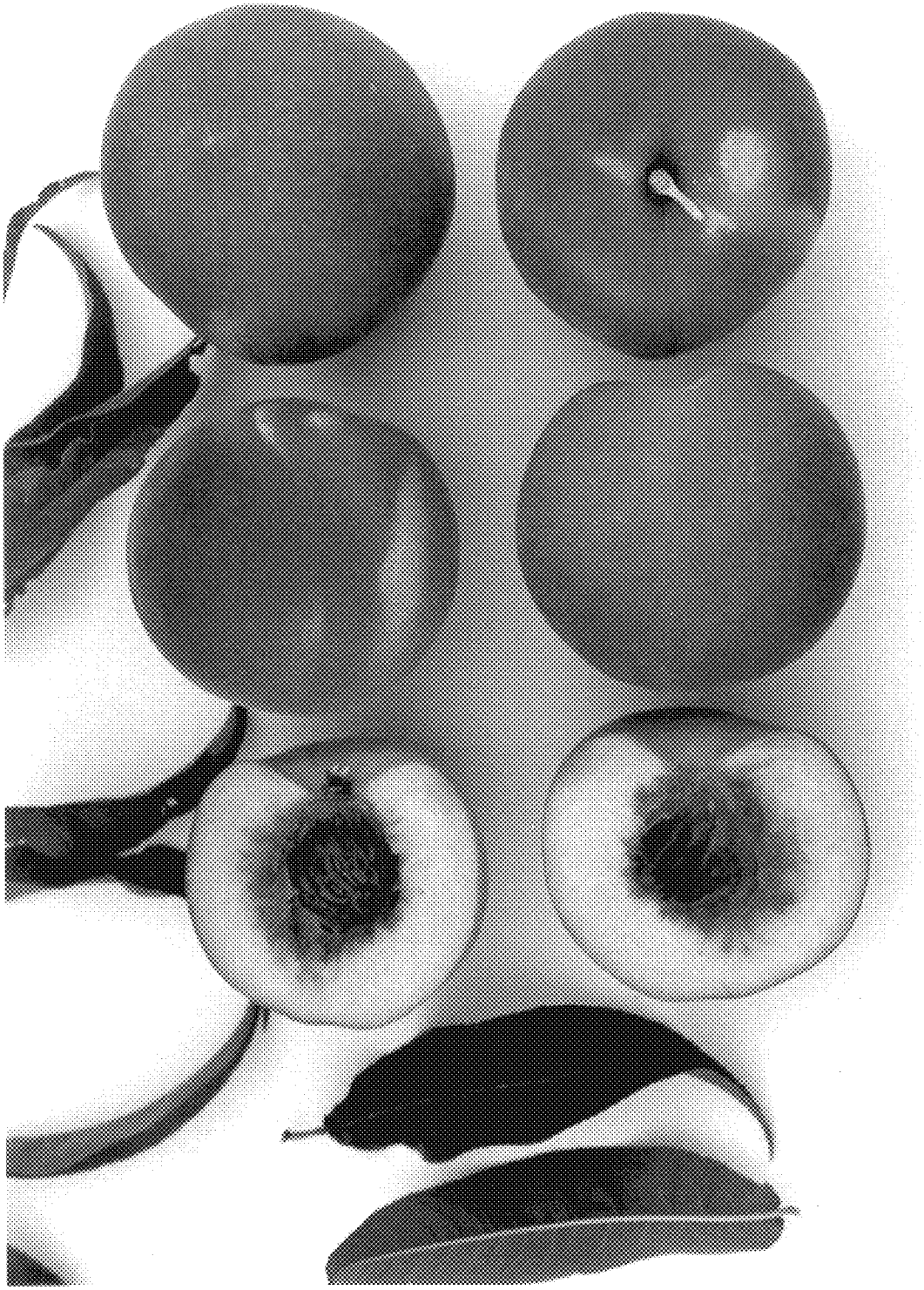

* * * * *